United States Patent [19]

Arita et al.

[11] Patent Number: 5,593,437
[45] Date of Patent: Jan. 14, 1997

[54] DEVICE FOR ADJUSTING A POSITION OF A FOCAL POINT OF AN INTRAOCULAR IMPLANT

[75] Inventors: Tatsuo Arita, Kumamoto; Ichiro Sakurai, Yatsushiro; Noboru Komiya, Kawasaki, all of Japan

[73] Assignee: Sakurai Seigi Company, Ltd., Kumamoto, Japan

[21] Appl. No.: 330,445

[22] Filed: Oct. 28, 1994

[30] Foreign Application Priority Data

Nov. 1, 1993 [JP] Japan .................... 5-297364

[51] Int. Cl.$^6$ .................... A61F 2/16; G02C 1/00; A61B 17/52
[52] U.S. Cl. .................... 623/6; 351/158; 600/9
[58] Field of Search .................... 623/6; 600/9; 351/41, 351/54, 158

[56] References Cited

U.S. PATENT DOCUMENTS

| | | | |
|---|---|---|---|
| 4,435,856 | 3/1984 | L'Esperance | 623/6 |
| 5,171,266 | 12/1992 | Wiley et al. | 623/6 |
| 5,326,347 | 7/1994 | Cumming | 623/6 |
| 5,389,981 | 2/1995 | Riach, Jr. | 600/9 X |

*Primary Examiner*—Mary Beth Jones
*Attorney, Agent, or Firm*—Koda and Androlia

[57] ABSTRACT

A device for adjusting a position of a focal point of an intraocular implant provided partially with a magnetic material and substituted for the crystalline lens and a magnetic flux generating spectacles for applying variable magnetism to the intraocular implant to attract the same so that the intraocular implant can be moved forward and backward with respect to the retina.

6 Claims, 12 Drawing Sheets

DEVICE FOR ADJUSTING A POSITION OF A FOCAL POINT OF AN INTRAOCULAR IMPLANT

BACKGROUND OF THE INVENTION

1. Field of the Invention

The invention relates to a method for adjusting focal point's positions of an intraocular implant and a device for the method, and more particularly to a method for adjusting focal point's positions of an intraocular implant, which is an artificial lens to be inserted in a human eyeball in place of crystalline lens extracted therefrom, and a device for use in the adjusting method.

2. Description of the Related Art

Human eyes essentially include eyeballs and optic nerve. These and appendages of eyeballs, i.e., eyelids, supercilium, conjunctiva, lacrimal apparatus and muscles of the eyeballs constitute the organ of vision. The outer wall of eyeballs comprises three layers of outer, middle and inner membranes, the outer membrane having cornea and sclera, the middle membrane having iris, ciliary body and choroid, and the inner membrane having retina. The eyeballs are filled substantially with a vitreous body and have crystalline lens before the vitreous body. A space between the crystalline lens and cornea is filled with aqueous humor.

The crystalline lens is an organ in the shape of biconvex lens and positioned centrally of the front half of the eyeball. Any objects placed near or far from human-eyes are focused into an image on the retina by the crystalline lens. For adjusting the crystalline lens to the objects near the eyes, ciliary muscle contracts to relax Zinn's zonule, which is in the shape of a flowery crown to sorround the crystalline lens, so that the crystalline lens becomes free of pulling by Zinn's zonule and increases in thickness due to elasticity of the crystalline lens itself. Thus, the adjusted crystalline lens can have the same function as of an optical lens of a short focal length. When the crystalline lens is adjusted to objects placed far from human eyes, ciliary muscle relaxes to tense Zinn's zonule, so that the crystalline lens is applied with a pulling force to be made thin and flat, thereby having the same function as an optical lens of a long focal length.

As above, the human eyes are exquisite, and the crystalline lens can be adjusted to the short or long range of scope by contracting or relaxing ciliary muscle to have separate focal point's positions and also to be increased or decreased in refraction factor as known.

Patients with cataracts suffer from troubles in eyesight by opacity of crystalline lens which has the above important function. Surgically extracting the opaque crystalline lens placed centrally of the front half of eyeballs is the only effective means for recovering the patients' eyesight at the present time. The eyes from which the crystalline lens is extracted and removed are the so-called "artificial aphakia" and cannot focus outside objects into images on retina at far distances (highly insufficient in refraction factor). Hence, merely extracting the opaque crystalline lens does, generally, not lead to recovery of good eyesight, and any lens means, such as spectacles or contact lens hitherto used, for supplementing the insufficient refraction factor is required to be applied. And now most widely made use of and popular is the method inserting an artificial lens into the eyes in place of crystalline lens extracted therefrom, i.e., use of the "intraocular implant" which enables recovery of eyesight to the extent nearest the inherent visual capacity.

Next, explanation will be given in more details with referring to FIGS. 17 to 21.

FIG. 17 is a cross-sectional view of a human eyeball, FIG. 18 a cross-sectional view of the same in normal vision, FIG. 19 a cross-sectional view of the same in near sightedness, FIG. 20 a cross-sectional view of the same in far sightedness, and FIG. 21 a cross-sectional view of the same wherein an intraocular implant is inserted.

In FIG. 17, 51 is cornea, a transparent membrane extending at the front of eyeballs and shaping a part of spheroid with radius of crook of about 8 mm. 52 is aqueous humor filled in the space between cornea 51 and crystalline lens 54. 53 is iris, a disc-like membrane equivalent to the diaphragm of cameras and having almost centrally a round hole (pupil) which is made smaller or larger corresponding to the amount of lights passing therethrough or by any other causes.

54 is a lens, having the most important function in the eyeball, and 55 is a ciliary body which causes the ciliary muscle to function for adjusting the crystalline lens 54 to focus at short and long ranges. It is known that the crystalline lens 54 in this instance does change curvature mainly on the front surface (at the side of cornea) but not on both surfaces, i.e., the front surface and the rear surface (at the side of retina).

57 is vitreous body made of a transparent sol substance filled, almost wholly in the eyeball, and refraction factor is 1.334. 58 is retina and 59 is optic nerve which transmits to cerebrum any signals of images focused on the retina 58.

FIG. 18 shows the focusing on retina in normal vision wherein any object placed far from the eye is focused into an image on retina. FIG. 19 shows the focusing in vitreous body before retina, i.e., the state of near sightedness wherein any two objective points spaced from each other at a very small distance cannot be sensed, just as two points, on the retina. In addition, FIG. 20 shows the focusing behind retina, the opposite of FIG. 19, i.e, the state of far sightedhess wherein distinct vision is not obtainable as in near sightedness shown in FIG. 19.

FIG. 21 is a cross-sectional view of an eyeball wherein opaque crystalline lens 54 causing visual disturbance is extracted and an intraocular implant is inserted. 60 is the in intraocular implant made of a polymeric material, and 61 is a loop for fixing the intraocular implant in position in the eyeball.

In the meantime, the aging society has increased the number of patients with cataracts, and of operations for extraction of the opaque crystalline lens and insertion of an artificial lens (intraocular implant) for recovery of eyesight.

The intraocular implant is made of a polymeric material, for example, polymethyl methacrylate A (PMMA) and has a fixed focus, so that the lens cannot freely focus at any positions on retina, as the crystalline lens of human eyes does from the so-called distance of distinct vision (scope in short range) to infinite vision (scope in long range). It is naturally possible in use of the intraocular implant for the subject to make his eyes half-shut or make pupil smaller so as to have higher focal depth, thereby improving his vision to a certain extent. But, this is limited due to the fixed focus of the intraocular implant. Furthermore, there has been such problem that the conventional intraocular implant can "supplement insufficient refraction factor" but not "adaptation capacity", the separate important function of crystalline lens, due to functional insufficiency of the intraocular lens in comparison with crystalline lens.

SUMMARY OF THE INVENTION

An object of the present invention is to provide an intraocular implant which is to be inserted into an eyeball after extraction of crystalline lens and is adjustable in positions forward and backward with respect to retina, thereby enabling the artificial lens to adjust focal length.

To achieve the above object, the method for adjusting a position of a focal point of intraocular implant according to the present invention provides such means that an intraocular implant provided partially with a magnetic material and substituted for crystalline lens is applied with magnetic flux at a high or low degree from the outside to move the intraocular lens forward and backward with respect to retina, thereby adjusting focal points of the lens.

In addition, to achieve the above object, the device for adjusting focal point's positions of intraocular implant according to the present invention provides such means as comprising an intraocular implant provided partially with a magnetic material and substituted for crystalline lens and a magnetic flux generating spectacles for applying magnetism at a high or low degree to the intraocular lens to attract the same, so that the intraocular lens can be moved forward and backward with respect to retina.

The intraocular implant lens according to the present invention may preferably be provided, at the outer peripheral part except the paraxial region, with an annular magentic material member or a magnetic thin film and provide a spring for urging the intraocular lens toward retina, and the magnetic flux generating spectacles has in the frame a coil through which controlled electric current is flowed.

The frame of the spectacles to be placed before the intraocular lens may be made of an annular magnetic material having a cross-section in a substantially rolled U-like shape and opening toward the lens, a winding wire being wound on the U-like shaped part, and an inner frame and an outer frame being tapered to their utmost ends, where the U-like shape of the cross section opens, to form magnetic poles at the utmost ends.

Furthermore, the frame of the spectacles before the intraocular lens may be provided with tubular fixed frames, a rotary frame fit thereto and a motor for driving the rotary frame, the tubular fixed frames and the rotary frame each having a magnetic material member, so that the rotary frame is turned at a predetermined rotation angle to adjust the magnetism to the intraocular lens.

Also, one of the temple portions of the spectacles may be provided with an infrared emitting part and the other with an infrared receiving part to detect a distance to an object and control the motor according to the detection results.

The curved surface or surfaces of the intraocular lens at one side or both sides thereof may be made aspherical to eliminate aberration on retina.

Further, bridging parts of a leaf spring which has freedom unidirectionally may form a damper so as to fix the intraocular lens radially inwardly of the damper.

The damper portions formed by the leaf spring's bridging parts placed radially outwardly thereof may be arranged almost in the middle of or between and with respect to the damper portions formed by the bridging parts placed radially inwardly of the spring.

The conventional intraocular implant-lens has a fixed focus and focuses only in a predetermined length. The present invention adjusts degrees of magnetic flux from the outside to generate attractive force and resiliency based on specific degrees of magnetic flux's attracting force or conversion of polarity of electric current flowing the coil, so that the intraocular lens pvodided with a magnetic material can be adjusted forward and backward with respect to retina without shifting from optical axis. Hence, the lens can be freely adjusted in focal point's positions from the distance of distinct vision (250 mm) to infinite vision.

Furthermore, focal point's positions from the distance of distinct vision to infinite vision can be automatically adjusted by manually changing the degrees of magnetic flux or detecting positions of any objects by use of infrared rays.

DETAILED DESCRIPTION OF THE PREFERRED EMBODIMENTS

Example 1

Figure 1:
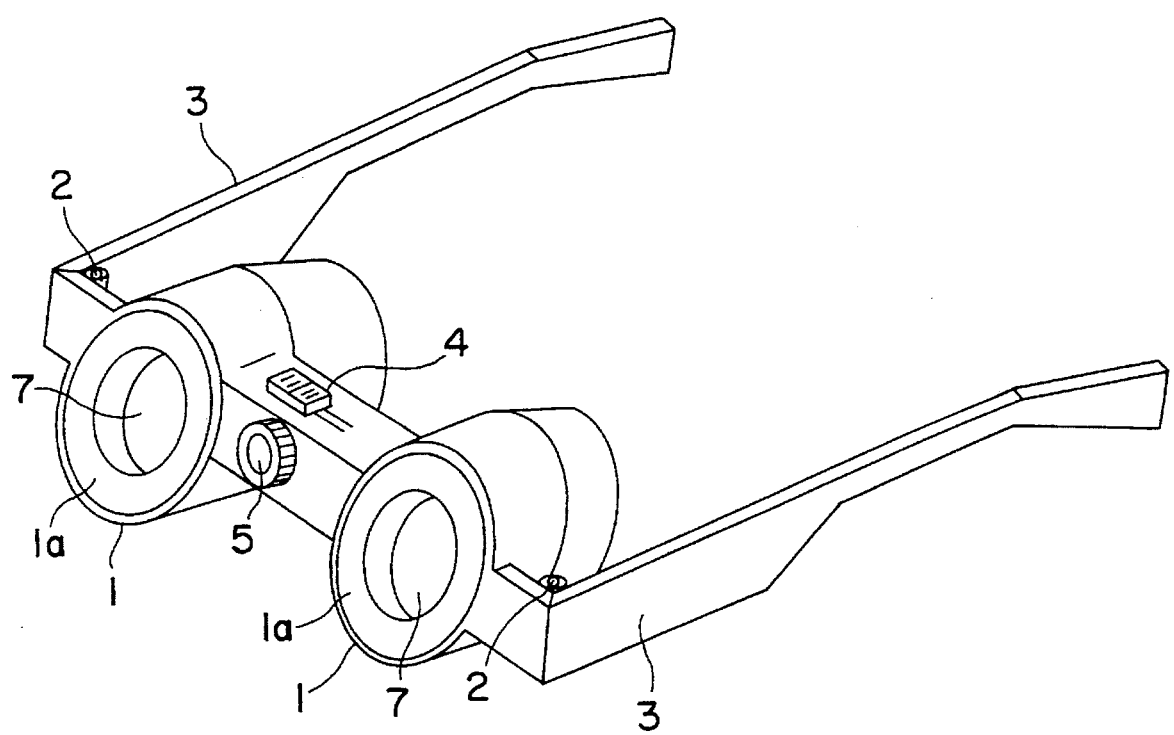
FIG. 1 is a perspective view of a magnetic flux generating spectacles, showing the method for adjusting focal positions of intraocular implant and the device for the method according to the present invention.

Next, a first example of the present invention will be detailed with referring to FIGS. 1 thruogh 6.

Figure 2:
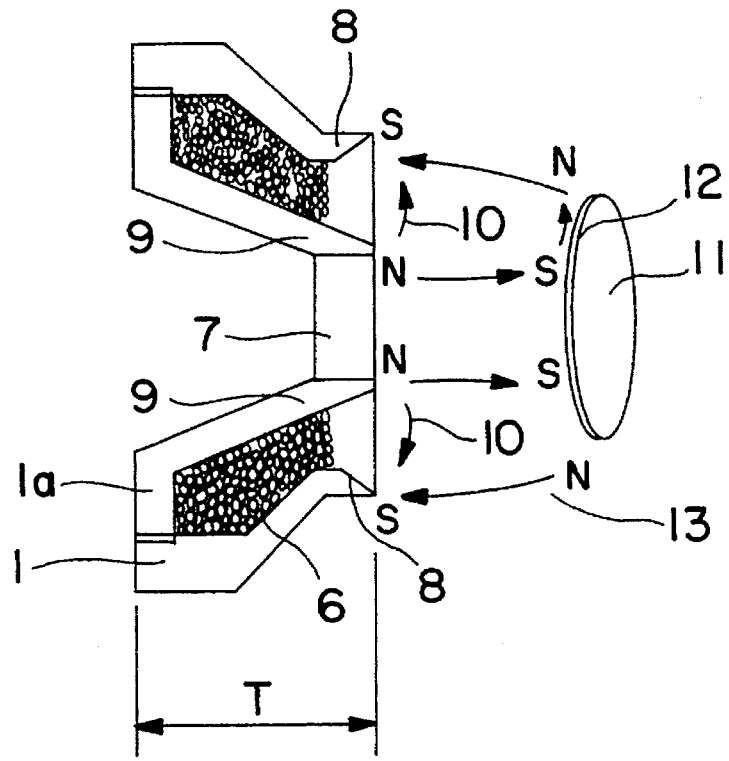
FIG. 2 is a partially sectional view of a magnetic flux generating part in the spectacles shown in FIG. 1.
Figure 3:
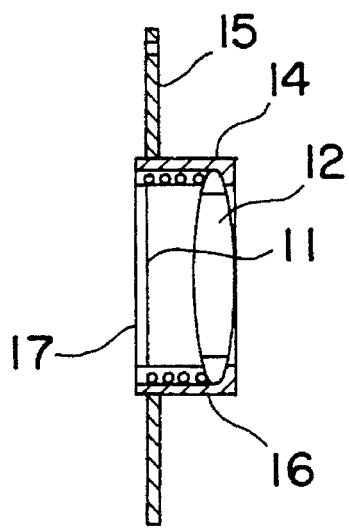
FIG. 3 is a sectional view of an intraocular implant and a mounting frame therefor.
Figure 4:
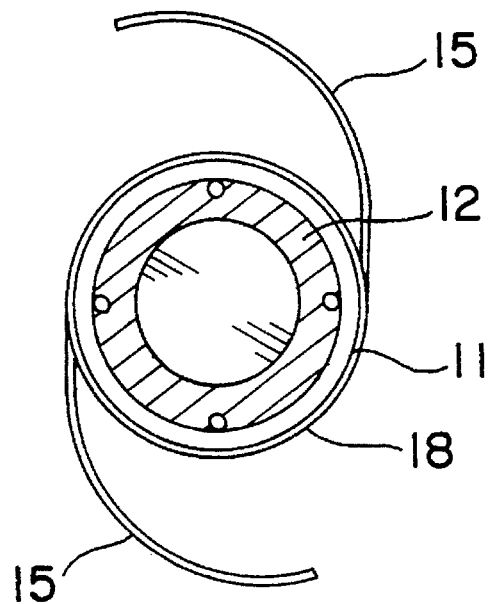
FIG. 4 is a front flew of the intraocular implant and the mounting frame shown in FIG. 3.
Figure 5:
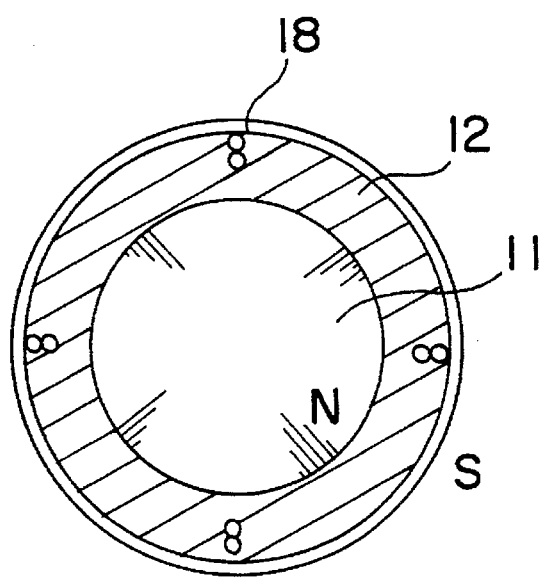
FIG. 5 is a diagram showing the structure of the intraocular implant.
Figure 6:
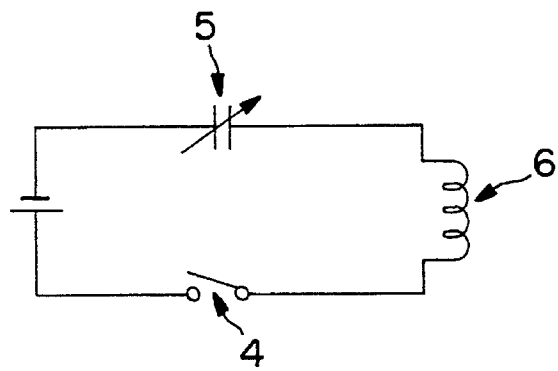
FIG. 6 is a diagram of an electric circuit for generating magnetic flux.

FIG. 1 is a perspective view showing a magnetic flux generating spectacles for adjusting the intraocular implant lens forward and backward with respect to retina. FIG. 2 is a longitudinally sectional view showing a part of the spectacles. FIG. 3 is a longitudinally sectional view showing a mounting frame portion for the intraocular lens. FIG. 4 is a front view of FIG. 3. FIG. 5 is a sectional view showing the structure of the intraocular lens. FIG. 6 is a diagram showing an electric circuit for moving the lens.

In FIGS. 1 and 2, 1 is an outer frame made of a soft magnetic material of high magnetic permeability, 1a an inner frame made of the same material as of the outer frame 1, 2 a hinge for supporting a temple 3 of the spectacles, 4 an ON/OFF switch for flowing electric current through a coil, and 5 a tuning knob serving also as a battery holder (See FIG. 6). Further, 6 is the coil, positioned between the outer and inner frames 1 and 1a, i.e., wound onto the inner frame 1a and covered with the outer frame 1, and 7 is a hollow part forming a passage for lights from the outside into an eyeball.

8 is a shape of the utmost end portion of the outer frame 1 and 9 is that of the inner frame 1a. In detail, the outer and inner frames 1 and 1a are pointed for concentrating the magnetic flux at maximum and tapered to the utmost ends as opened outwardly, so that leakage of magnetic flux from the outer frame 1 to the inner frame 1a can be reduced and magnetic flux can be concentrated onto a magnetic material member 12 provided on the peripheral part of an intraocular lens 11 except a paraxial region. The magnetic material member 12 may use a hard magnetic material or a soft magnetic material of high permeability and may be in an annular shape surrounding the intraocular lens. Alternatively, the magnetic material member 12 may use a thin film deposited on the intraocular lens at its peripheral part except the paraxial region (all the drawings FIGS. 2 through 5 show the magnetic thin film). Shown in FIG. 2 are a sectional view of a magnetism generating part in the spectacles, a section of the intraocular lens and a circuit of magnetism.

In the shown structure, magnetic flux flows from the utmost end of the outer frame 1, through the magnetic material member 12 on the intraocular lens, to the utmost end of the inner frame 1a. 13 designates flow of effective magnetic flux in this case. 10 designates flow of leaked magnetic flux. The tapering of the utmost ends of the outer and inner frames 1 and 1a are provided for reducing leakage of magnetic flux 10 from the outer frame 1 directly to the inner frame 1a. It is preferable to reduce the leakage of magnetic flux 10 as much as possible.

FIG. 3 shows the structure of the intraocular lens unit according to the present invention and FIG. 4 shows a cross-section of the lens. 14 is a frame supporting the intraocular lens 11 and made of non-magnetic material. The frame 14 has a non-magnetic spring 16 always urging the lens 11 in a predetermined direction, and a non-magnetic fixing ring 17. 15 is a loop for fixing the intraocular lens unit in an eyeball. 18 is small through bores which opened in the intraocular lens and used for setting the lens in a predetermined position upon operation.

Next, FIG. 5 shows a section of the intraocular lens 11 in which a magnetic thin film 12 is deposited on the surface surrounding the paraxial region through which lights pass. The magnetic thin film may be formed by a sputtering process and use a soft magnetic film, such as Sendust (Fe-Al-Si) or Permalloy (Fe-Ni), or a hard magentic material, such as Fe-Co-Ni.

Also, an annular magnetic material may be provided in place of the magnetic thin film 12 and use a magnetic material of high permeability or an annular magnet, in turn, a hard magnetic material.

To prevent chemical reaction of the deposited magnetic thin film or annular magnetic material on the intraocular lens with respect to intraocular tissues such as vitreous body 57, the whole of lens may be protected by a sputtered film, such as SiO, $SiO_2$, or the like. Further, the magnetic film made of the hard magnetic material or the annular magnetic material are magnetized, for example, with the inner peripheral part being a south pole and the outer peripheral part being a north pole. And the direction of winding wire 6 is set to allow the utmost end 8 of outer frame 1 to have south pole, and also allow the utmost end 9 of inner frame 1a to be north pole. (See FIG. 2, the polarity may be reversed.)

FIG. 6 shows an electric circuit for moving the intraocular lens forward and backward with respect to retina. The circuit is assembled in the spectacles as foregoing.

Next, movement of the intraocular lens will be detailed.

An intraocular implant to be inserted into an eyeball after extraction of crystalline lens having troubles due to cataract or the like is made of a polymeric material, for example, polymethyl methacrylateA (PMMA). And pupil is generally 2–5 mm in diameter and crystalline lens is about 10 mm in diameter. The intraocular implant substituting for crystalline lens is about 7 mm in diameter (lens body). Furthermore, the thickness of crystalline lens is generally 4 mm and is said to change in a range from 3.7 to 4.4 mm by adjustment of vision in short and long ranges. That is, the crystalline lens is to be regarded as a thick lens in geometric optics.

Next, the focal length of crystalline lens will be calculated.

Figure 7:
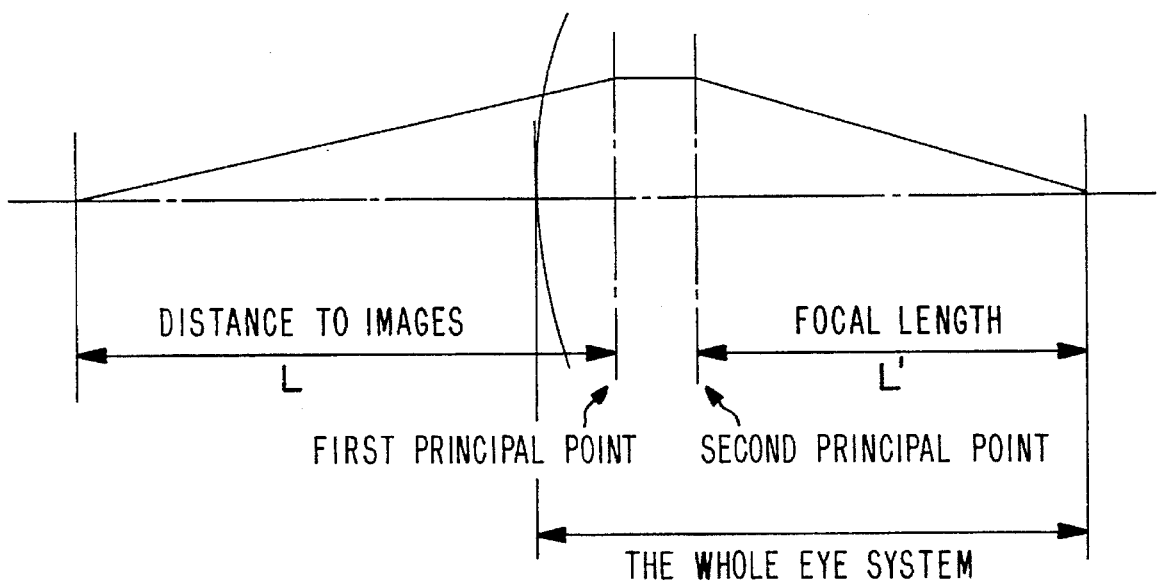
FIG. 7 is a diagram showing image formation by paraxial ray.

FIG. 7 shows a diagram for focusing with paraxial rays in a thick lens, wherein L is a distance to an object, i.e., between distance of distinct vision (250 mm, vision in short range, distance from eyes reading books, etc) and distance of infinite vision (vision in long range), and L' is rear focal length from the second principal point to retina in the whole eye system, about 22.8 mm.

Focal length f is represented by the following formula.

$$\frac{1}{f} = \frac{1}{L} + \frac{1}{L'}$$

In case that L is 250 mm or infinite (∞) and L' is 22.8, f is 20.9 mm when L is 250 mm and 22.8 mm when L is infinite, and the difference of f is 1.9 mm.

In detail, when an intraocular lens is applied in place of crystalline lens, if the crystalline lens and the intraocular lens have the same refraction factor, any objects spaced 250 mm or more from eye will be accurately focused into an image on retina by adjusting position of the intraocular lens at 2.0 mm at maximum (1.9 mm in calculation) with respect to retina.

The present invention provides the outside adjustment of intraocular lens' positions with respect to retina. As seen in the electric circuit shown in FIG. 6, the switch is turned on to cause current from the battery to flow through the coil while being controlled of flow, so that the utmost ends of the outer frame 1 and the inner frame 1a each made of soft magnetic material have magnetic poles, for example, south pole at the outer frame 1 and north pole at the inner frame 1a. And the intraocular lens when using a soft magnetic material has a north pole on the outer peripheral part and a south pole on the inner peripheral part, so that the south and north poles attract mutually corresponding to specific degrees of magnetic flux from the outside, thereby moving the intraocular lens.

Similarly, in case that the magnetic material used on the peripheral part of the intraocular lens is a hard magnetic material, when the outer and inner peripheral parts are each preliminarily set to have a north pole and a south pole, respectively, the same effect as above can be obtained. In detail, the intraocular lens is attracted by a pole on which magnetic flux is generated, so that the lens is moved intraocular lens is usually placed nearer the retina by the non-magnetic spring to be in the state of long range vision. The lens when attracted is brought into the state of short range vision. The amount of movement of the lens can be set to a predetermined distance by correlation of magnetic flux's attracting force and the force of non-magnetic spring.

The intraocular lens according to the present invention is basically biconvex and spherical. But, there is a problem of aberration of images at the periphery of visual field since the eyes when regarded as an optical system (the whole eye system) comprises a thick lens, functions in the paraxial region and includes retina in a spherical shape. To solve the problem, one or both sides of the biconvex intraocular lens may be made aspherical, and curvature of the aspherical surface of the lens with respect to retina is set in consideration of the amount of movement of the lens, whereby aberration of the intraocular lens on the retina can be eliminated.

Furthermore, generally, there are many people who do not want to use spectacles for near-sightedness, far-sightedness or multi-focus by reason that they feel uneasy about others' attention to their wearing spectacles, they do not fully understand necessity of spectacles, or they have never enjoyed merits of spectacles of proper degrees. Also, persons who usually use spectacles have such complaints as "the spectackles is heavy", "I feel pain on the nose", etc. Hence, the magnetism circuit part of the magnetic flux generating spectacles shown in FIG. 1 is required to be made as thin, light and good-looking as possible.

Example 2

Figure 8:
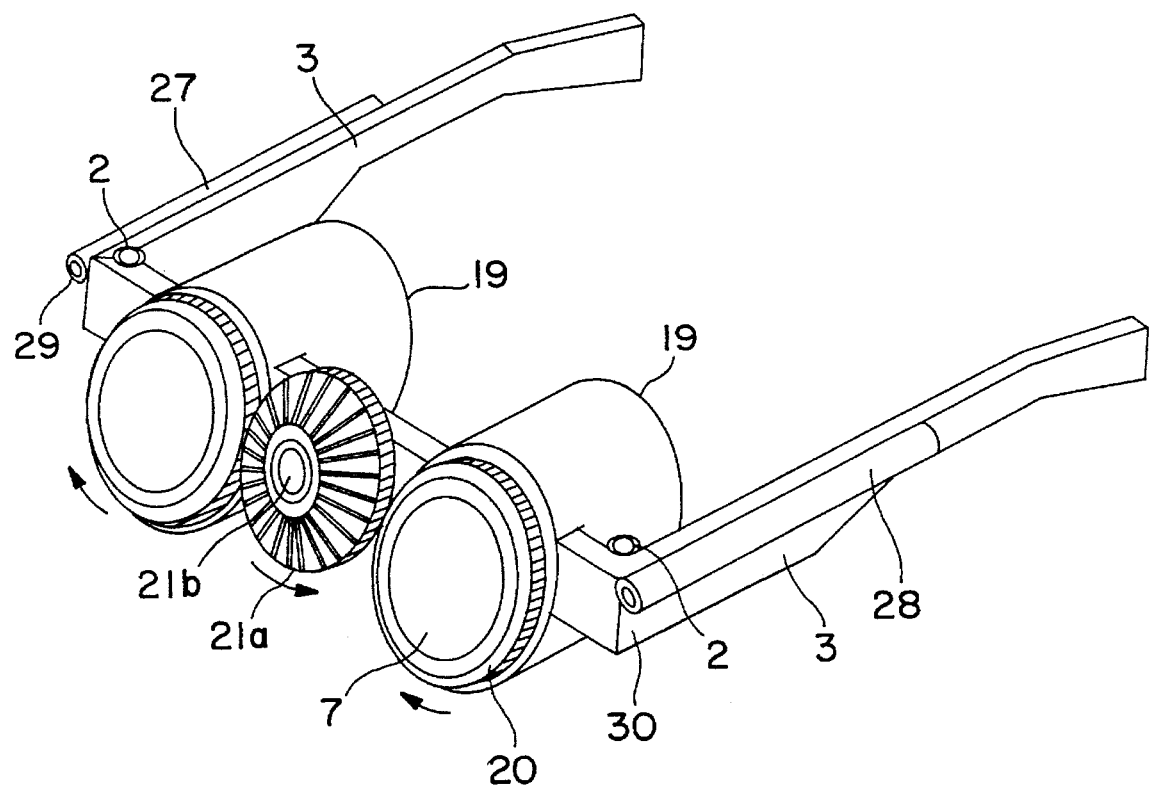
FIG. 8 is a perspective view of a magnetic flux generating spectacles in another example of the invention.
Figure 9:
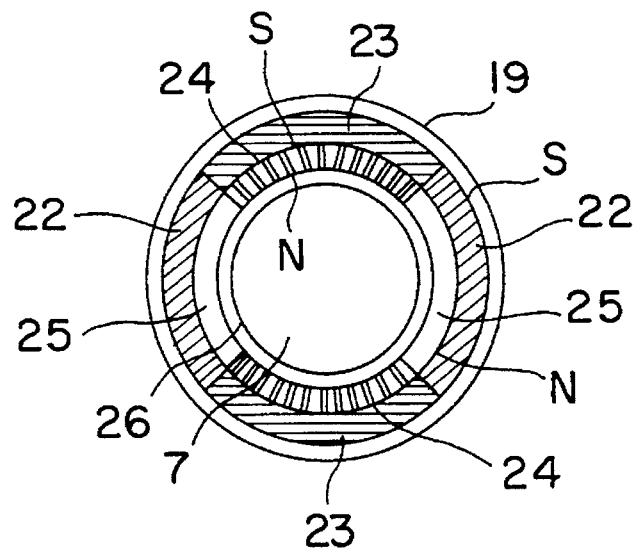
FIG. 9 is a cross-sectional view taken at the outer tube portion in the FIG. 8 example.
Figure 10:
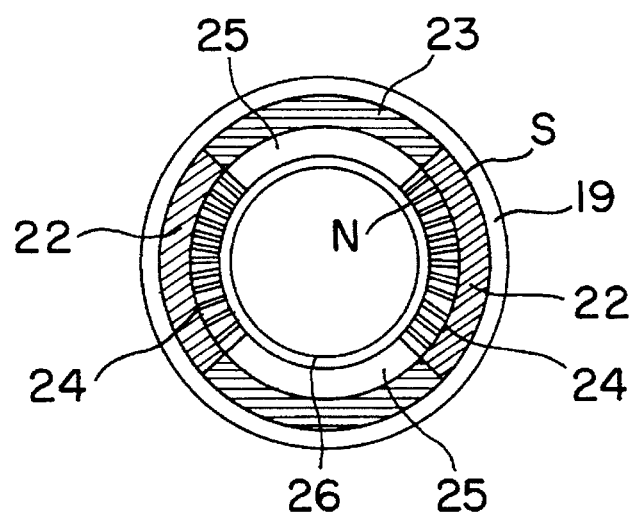
FIG. 10 is a cross-sectional view showing the same in FIG. 9 where the rotational angle is changed.

The example will be detailed with referring to FIGS. 8, 3, 4, 5, 9, 10 and 11. The intraocular lens components shown in FIGS. 3–5 used in this example is the same as of Eample 1 and not referred to here. FIG. 8 is a perspective view of a magnetic flux generating spectacles used in Example 2, and FIGS. 9 and 10 are sectional view of the outer tube 19. The outer tube 19 shown of appearance in FIG. 8 is made of non-magnetic material in a cylindrical shape and coupled with a temple 3 by a hinge 2.

20 is a front end of an inner tube fit into an outer tube 19 and has a geared part on, the periphery. 21a is a rotation-adjuster gear, and 21b a main rotary shaft of a motor. The rotation-adjuster gear 21a is meshed with the inner tube front end 20, so that the main rotary shaft 21b is rotated to turn the inner tube 20 at a predetermined angle in the direction indicated by the arrow.

FIG. 9 shows a structure of the outer tube 19 in section. 22 is a hard magnetic material member fixed in the outer tube 19 and arranged symmetrically with respect to the axis of the outer tube 19 at an angular space of 90° from a longitudinal central plane thereof. 23 is a member made of non-magnetic material fit in a chamfered part of the outer tube, having the same peripheral surface as of and machined together with the member 22 for improving accuracy of circularity of their inner periphery. Also, 24 is a member made of a hard magnetic material fixed on an inner tube 26 and arranged symmetrically with respect to the axis of the inner tube 26 at an angular space of 90° from a longitudinal central plane thereof. The member 22 of hard magnetic material on the outer tube 19 and the member 24 of hard magnetic material on the inner tube 26 make a cylindrical formation with stepped portions with respect to the the member 23 of non-magnetic material on the outer tube 19.

25 is a chamfered part of the hard material member 24 of the inner tube 26. The chamfered part may be hollow or filled with non-magnetic material. The outer peripheral surface of the member 24 is machined along the axis of the inner tube 26 to have excellent accuracy of circularity and a small clearance against the machined inner surface of the outer tube 19 and allow the inner tube 26 to be applied with reduced load in rotation.

FIG. 10 shows the state that the inner tube 26 is turned 90° with respect to the outer tube 19 in FIG. 9. As the inner tube 26 is turned, the fixed member 24 of hard magnetic matrial overlaps with the hard magnetic material member 22 on the outer tube 19. In other words, the couples of the member 22 and member 24 and those of the member 23 and 25 are each symmetrically positioned with respect to a longitudinal central plane of the outer tube 19. Four chamfered parts are provided in the example by circumferential division into four parts but may be larger in number.

The component 27 on the temple 3 of spectacles shown in FIG. 8 is an emitting part of infrared rays, and 28 is a corresponding receiving part for receiving infrared rays which emitted from the emitting part 27 in parallel to each other, met against any objects and reflected.

Figure 11:
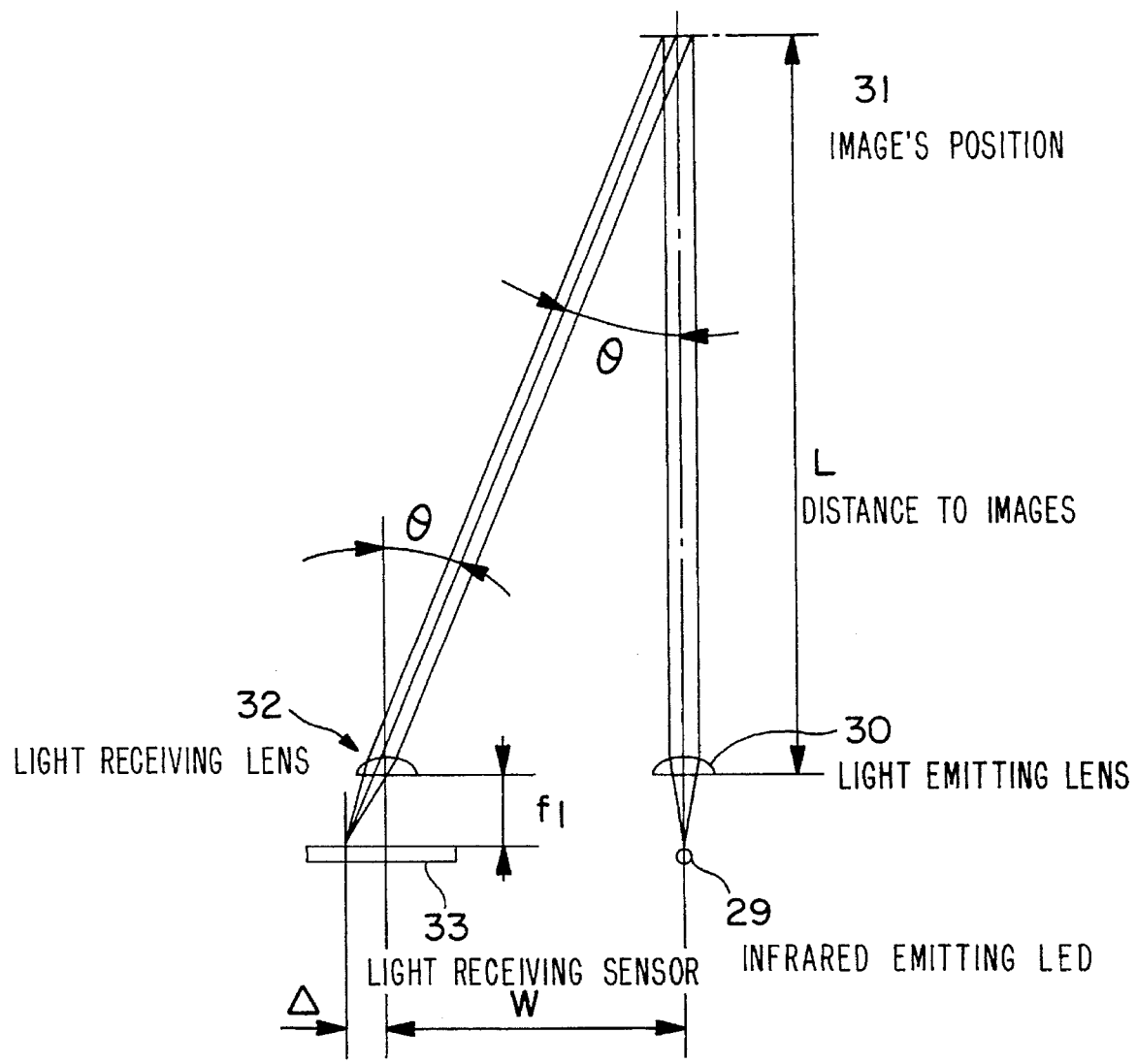
FIG. 11 is a diagram of an optical path for measuring distances.

FIG. 11 shows an optical path for measuring distances. 29 is LED for generating infrared rays, 30 a light emission lens, L a distance to any object, and 31 a position of the object. 32 is a light reception lens and 33 is a light reception sensor. Additionally, $f_1$ is focal length of the light reception lens 32.

The distance to the image of object in use of the magnetic flux generating spectacles is optically determined, and the foregoing inner tube 26 is turned at a predetermined angle so as to automatically focus on the image.

Very small variables $\Delta$ representing distances to the image can be obtained by the following formula.

$$\text{Tan}\theta = \frac{W}{L}$$

$$\Delta = f_1 \cdot \text{Tan}\theta = \frac{f_1 \cdot W}{L}$$

$$\therefore L = \frac{f_1 \cdot W}{\Delta}$$

wherein $f_1$, and W are known values, and $\Delta$ is variables which correspond to L and are measured values, so that L will be determined when values of $\Delta$ are obtained.

Next, functions according to this example will be detailed.

First, magnetization is applied from the inside of the hard magnetic material member of the inner tube to the outside of the hard magnetic material member of the outer tube having a south pole at the outer side and a north pole at the inner side. That is, the circumferentially outside of the device in FIG. 9 has south pole and the inside north pole. Hence, when the intraocular lens has north pole at the outer periphery side and south pole at the inner periphery side, magnetic flux extends from the inner periphery of spectacles to the inner peripheral side of the hard magnetic material member on the lens component, and to the outside of spectacles, so that the lens is attracted. Furthermore, in FIG. 10, a region generating magnetic flux between the hard magnetic material member fixed on the outer tube and that fixed on the inner tube is reduced to half to make smaller the attractive force between that region and the hard magnetic material member on the intraocular lens, so that the attractive force is balanced with the resilience of the ceramic spring to be adjustable corresponding to the angle of rotation of the hard material member of the spectacles, thereby enabling the intraocular lens to be adjusted in positions with respect to retina.

The angle of rotation of the hard material member of spectacles is transmitted to the inner tube by the rotation-adjuster gear through a predetermined amount of rotation of the main rotary shaft of the motor placed centrally of the spectacles and according to the automatic distance measurement method wherein a distance to any objects is optically determined by use of infrared rays emitted from the device mounted to the temple of the spectacles. Hence, distinct vision of any objects at predetermined positions is enabled. Also, it is possible to dispose a rotation actuator for the main rotary shaft of motor between the inner frame and outer frame of the spectacles so as to apply rotation angles to the inner frame.

The intraocular lens having on the surface a thin film made of a soft magnetic material as shown in Example 1 can be applied to Example 2. Furthermore, the soft magnetic material thin film on the surface of the intraocular lens with the thin film illustrated in FIGS. 2–5 provided at the side of the lens nearer cornea may alternatively be formed at the side nearer retina or at both sides of the lens.

Additionally, a hard magnetic film may be provided on the intraocular lens in place of the soft magnetic film. And An annular soft magnetic material member of high permeability can be effectively used in place of the annular hard magnetic material member disclosed in this Example 2.

Example 3

This example relates to a fixing method of the intraocular lens according to the present invention and is a modified embodiment of the lens fixing method referred to in FIGS. 3 and 4.

Figure 12:
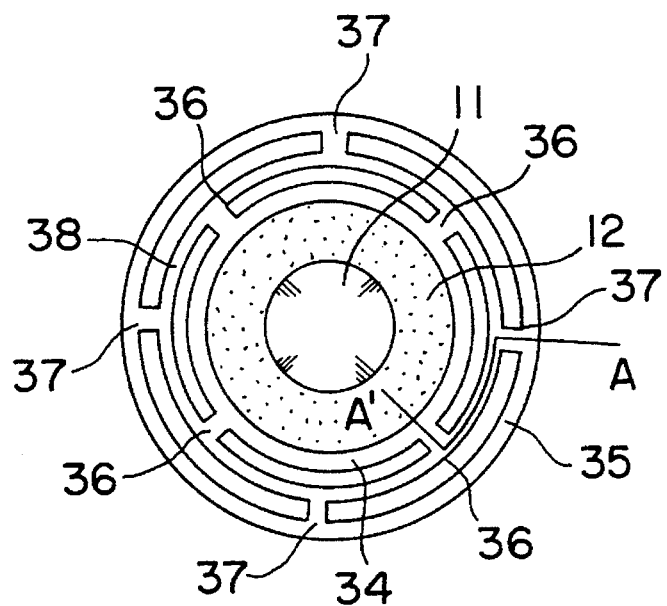
FIG. 12 is a plan view showing a method for fixing the intraocular implant.
Figure 13:
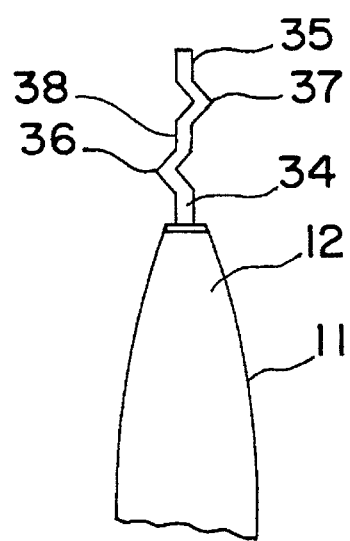
FIG. 13 is a sectional view of the same in FIG. 12.
Figure 14:
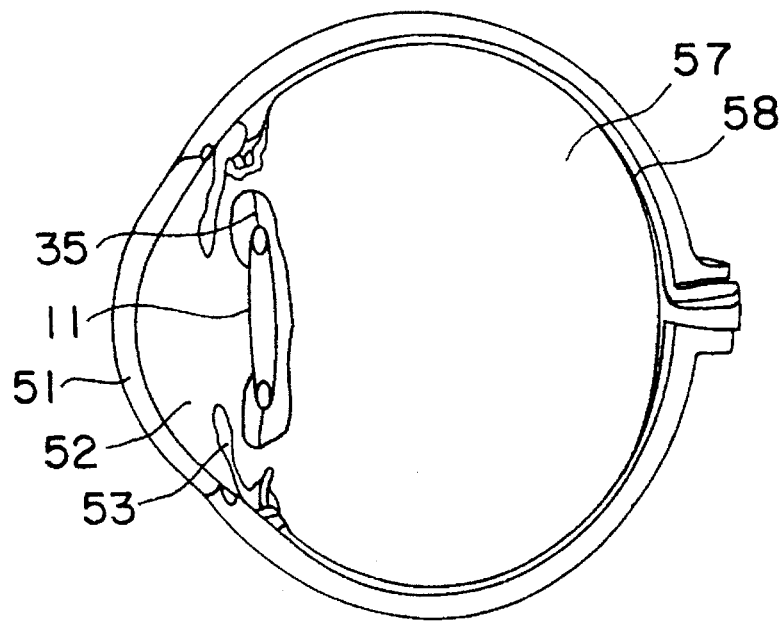
FIG. 14 is a sectional view of a human eye ball wherein an intraocular implant is applied, showing a configuration of the intraocular implant at a position.
Figure 15:
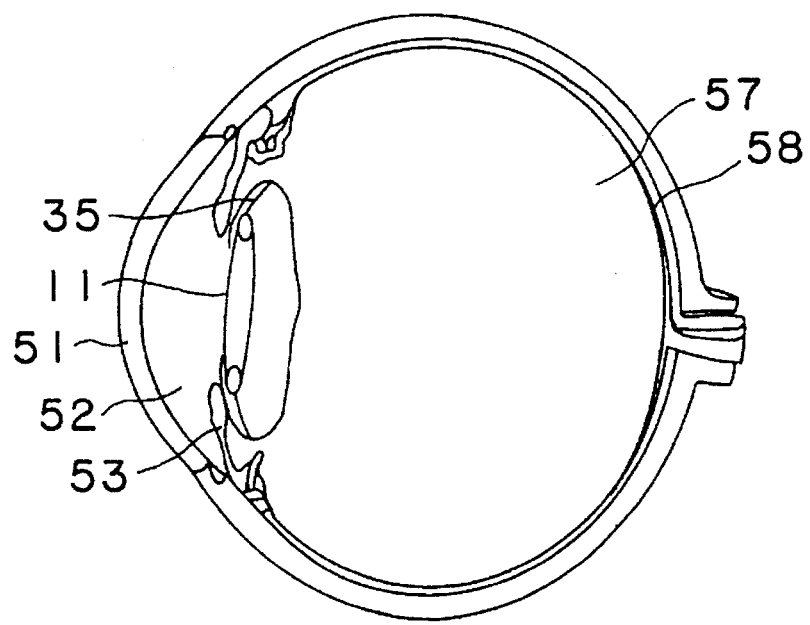
FIG. 15 is a sectional view of the same in FIG. 14, showing another configuration of the intraocular implant at another position.
Figure 16:
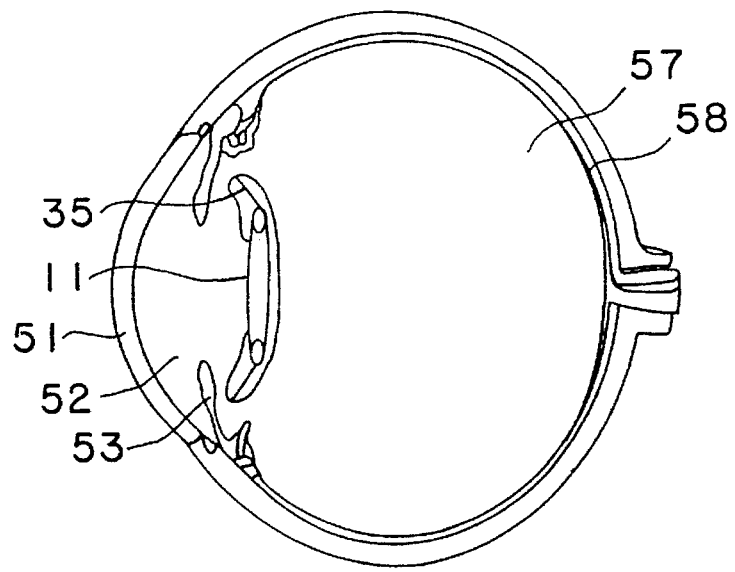
FIG. 16 is a sectional view of the same in FIG. 14, showing a further different configuration of the intraocular implant at a further different position.
Figure 17:
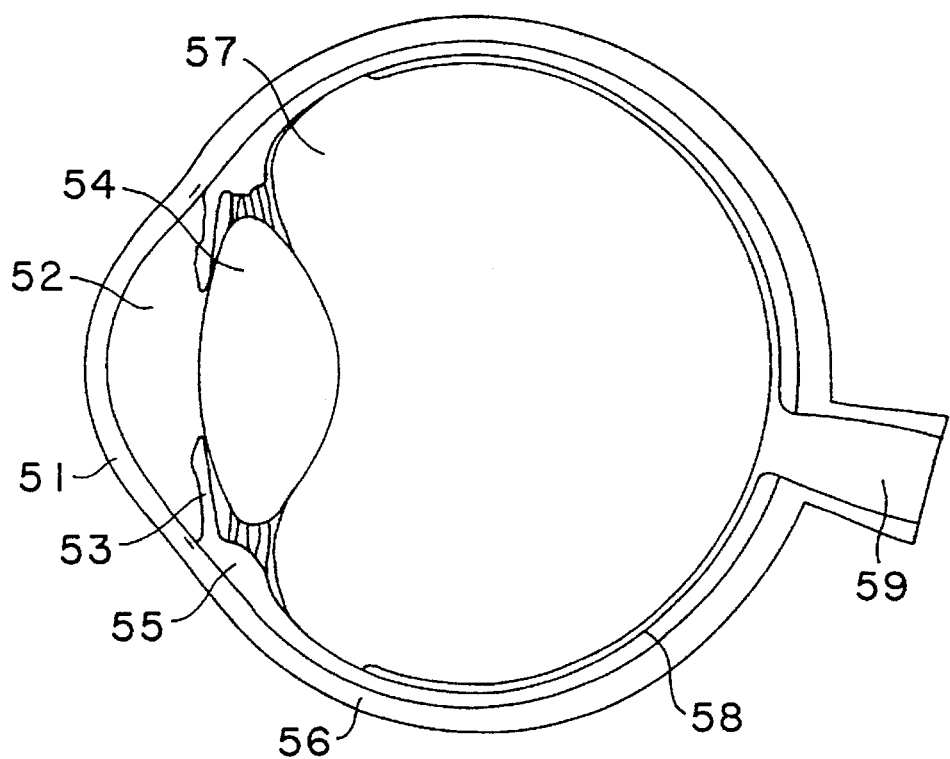
FIG. 17 is a sectional view of a normal human eye ball.
Figure 18:
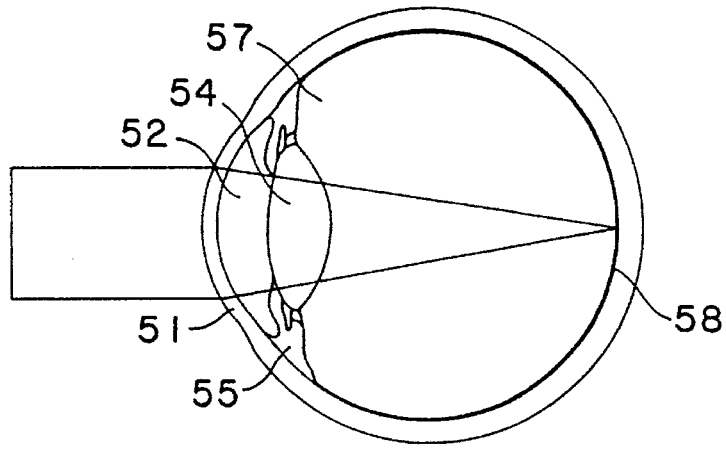
FIG. 18 is a sectional view of the human eye ball in normal vision.
Figure 19:
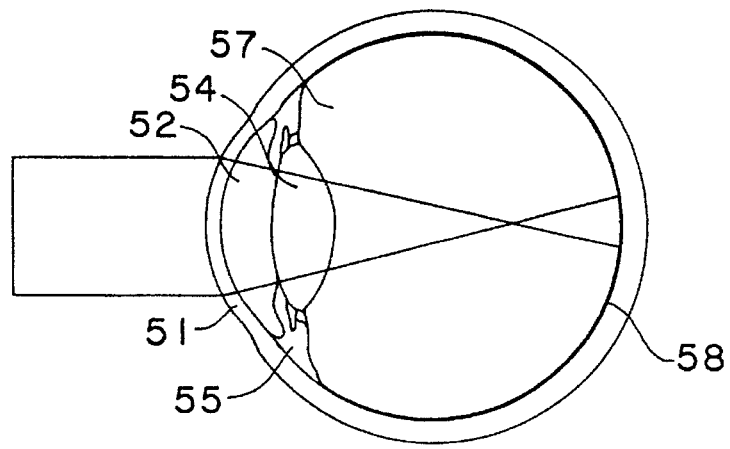
FIG. 19 is a sectional view of the human eye ball in near sightedhess.
Figure 20:
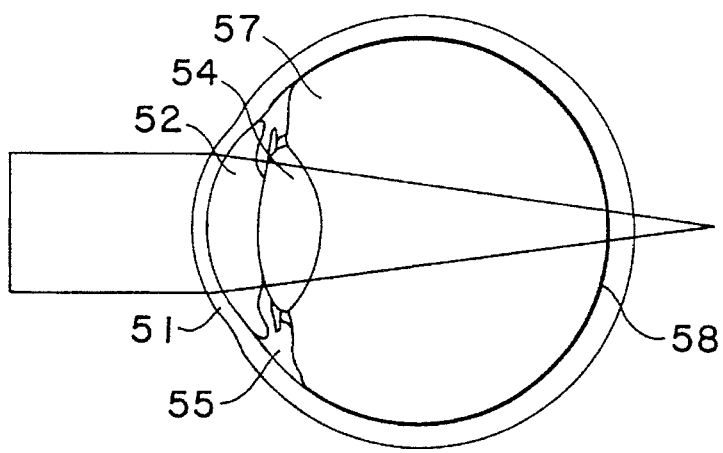
FIG. 20 is a sectional view of the human eye ball in far sightedness.
Figure 21:
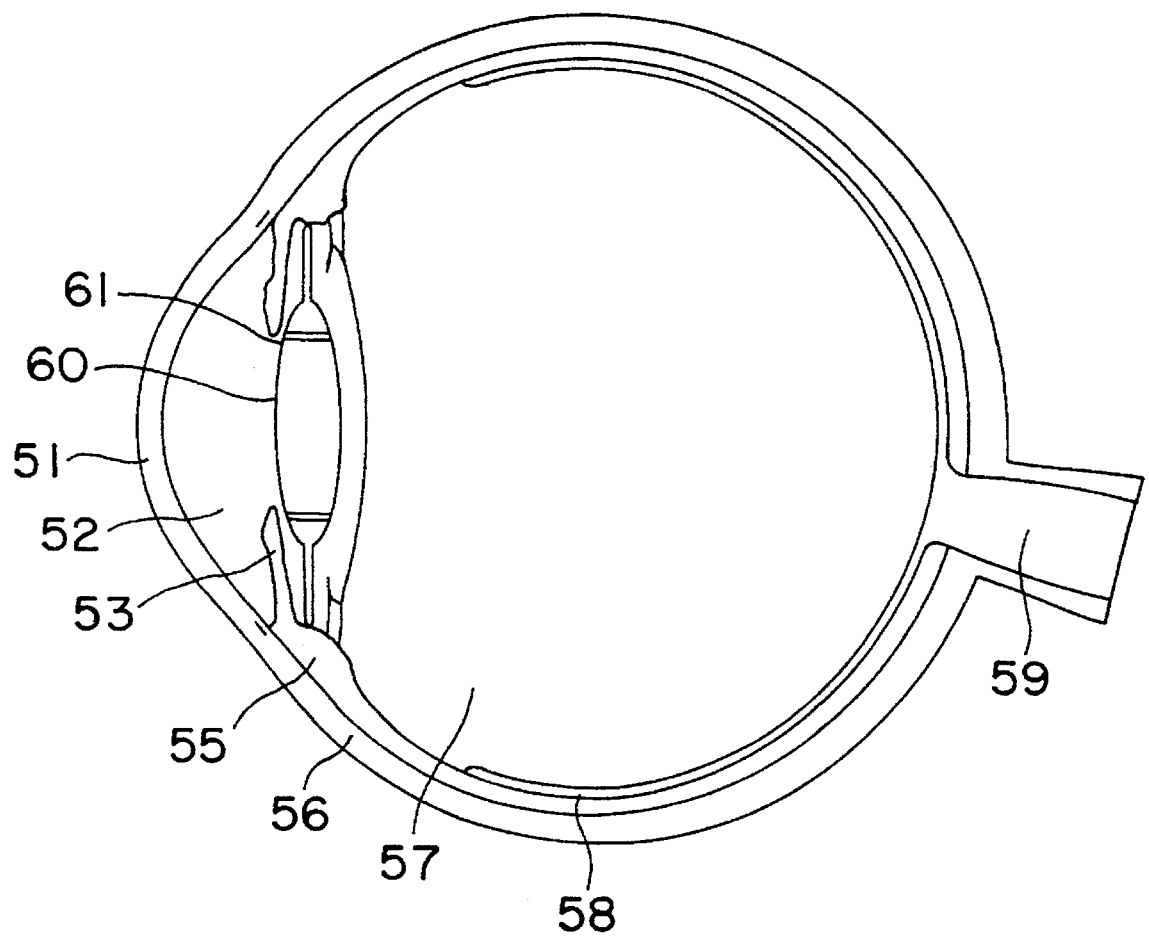
FIG. 21 is a sectional view of the human eye ball wherein an intraocular implant is inserted.

Example 3 will be detailed with referring to FIGS. 12 to 16. FIG. 12 is a plan view of the lens fixing method, FIG. 13 a sectional view of the same. FIGS. 14, 15 and 16 are sectional views showing the three states of the device (FIG. 12) fixed to the intraocular lens.

In FIG. 12, 34 is an inner frame of leaf spring for fixing the intraocular lens, and 35 is an outer frame of leaf spring for fixing the spring in an eyeball. 36 is four inner bridges which connect the inner frame 34 with a middle frame 38 of the spring, and 37 is four outer bridges which connect the middle frame 38 with the outer frame 35. In FIG. 13, the four inner bridges 36 and four outer bridges 37 project leftward and rightward, respectively as shown, serving as a damper. In contrast with a so-called gimbal having two bridges to remove rolling and pitching, the present invention uses four bridges in an unidirectionally movable leaf spring for preventing the central part of intraocular lens from shifting from optical axis, the inner and outer four bridges serving as the damper for readily reacting with magnetic flux from the outside. The leaf spring which is movable unidirectionally is made of non-magnetic material.

FIGS. 14 to 16 shows three modes of the intraocular lens mounted by use of the foregoing unidirectionally movable leaf spring. FIG. 14 is the state that the intraocular lens is moved toward cornea, i.e., in the state of near-sightedness, FIG. 15 the state that the lens mounted to the leaf spring is subjected to no force from the outside, and FIG. 16 the state that the lens is moved toward retina, the state of far-sightedness.

Next, functions of the intraocular lens using the magnetic flux generating spectacles of Example 1 and the unidirectionally movable leaf spring of Example 3 will be detailed. In detail, when the intraocular lens is provided on the surface with a hard magnetic material member or deposited with hard magnetic thin film to thereby have, for example, a south pole at the inner peripheral part and a north pole at the outer peripheral part (see FIG. 2), and electric current is caused to flow through the coil to allow the utmost end of the outer frame of the spectacles to have south pole and that of inner frame to have north pole, attractive force functions at the poles to move the intraocular lens toward cornea as shown in FIG. 14. When the current in the coil of the spectacles is off, the leaf spring mounting the lens is brought into a normal state to be positioned at the middle position as shown in FIG. 15. When the direction of current flow in the coil is changed reversely, to that in FIG. 14, the utmost end of the outer frame of magnetic flux generating spectacles has north pole and that of the inner frame south pole, which polarity correspond to those of the hard magnetic material member on the lens and they repel to each other, thereby moving the intraocular lens toward retina.

As seen from the above, polarity of current flowing in the coil is changed to move the intraocular lens toward cornea or retina.

Conventionally, when crystalline lens is extracted from an eyeball and an intraocular lens is inserted therein, the hollow part 7 of the magnetic flux generating spectacles is applied with an additional spectacles using a continouous focal conversion lens. The present invention does not need to use such additonal device except in the cases of astigmatism and can be used with the hollow part 7 being kept as it is. Hence, there is caused no problems such as "frost" on the lens when the user goes into a warm room from the cold outdoors.

Additionally, there is no need to clean any finger-print or stain adhered on the lens.

As seen from the above, according to the present invention, the notable effect that adjustment of focal length which is impossible conventionally can be achieved is obtainable by providing a magnetic material on the intraocular lens and applying thereto specific degrees of magnetism.

Detection of positions of any objects by use of infrared rays and application of detected values to the foregoing adjustment of focal length achieve the effect of automatic adjustment of focal length.

Also, the magnetic flux generating spectacles does not need to use an additional lens except the cases of astigmatism, thereby providing the additional effect of eliminating troubles from cleaning frost or stain on the additional lens.

What we claimed is:

1. A device for adjusting a position of a focal point of an intraocular implant comprising an intraocular implant provided partially with a magnetic material and a magnetic flux generating spectacles for applying variable magnetism to the intraocular implant to attract the same, so that the intraocular implant can be moved forward or backward with respect to the retina, wherein the intraocular implant is at the outer peripheral part except the paraxial region, provided with said magnetic material and a spring is provided for urging the intraocular implant toward the retina, and the flux generating spectacles has in the frame a coil through which a controlled electric current is flowed and further the frame of the spectacles to be placed before the intraocular implant is made of an annular magnetic material having a cross section in a substantially rolled U-like shape and opening toward the implant, a winding wire is wound on the U-like shaped part, and an inner frame and an outer frame is tapered to their utmost ends, where the U-like shape of the cross section opens, to form magnetic poles at the utmost ends.

2. A device for adjusting a position of a focal point of an intraocular implant comprising an intraocular implant provided partially with a magnetic material and a magnetic flux generating spectacles for applying variable magnetism to the intraocular implant to attract the same, so that the intraocular implant can be moved forward and backward with respect to the retina, wherein the frame of the spectacles before the intraocular implant is provided with tubular fixed frames, a rotary frame fitted thereto and a motor for driving the rotary frame, the tubular fixed frames and the rotary frame each having a magnetic material member, so that the rotary frame is turned a predetermined rotation angle to adjust magnetism to the intraocular implant.

3. A device for adjusting a position of a focal point of an intraocular implant as set forth in claim 2, wherein one of the temple portions of the spectacles is provided with an infrared emitting part and an other of the temple portions is provided with an infrared receiving part to detect a distance to an object and control the motor according to the detection results.

4. A device for adjusting a position of a focal point of an intraocular implant as set forth in claim 2, wherein the intraocular implant has one curved side which is aspherical.

5. A device for adjusting a position of a focal point of an intraocular implant comprising an intraocular implant provided partially with a magnetic material and a magnetic flux generating spectacles for applying variable magnetism to the intraocular implant to attract the same, so that the intraocular implant can move forward or backward with respect to the retina, wherein said implant is provided with a leaf spring and bridging parts of said leaf spring move unidirectionally and form damper portions so as to fix the intraocular implant radially inwardly of the damper portions.

6. A device for adjusting a position of a focal point of an intraocular implant as set forth in claim 5, wherein the damper portions formed by the leaf spring's bridging parts placed radially outwardly of the intraocular implant are arranged substantially in the middle of damper portions formed by the bridging parts placed radially inwardly of the spring.

* * * * *